United States Patent
Matsumoto (10) Patent No.: US 8,137,617 B2
(45) Date of Patent: Mar. 20, 2012

(54) THIN FILM HEATER AND ANALYTICAL INSTRUMENT

(75) Inventor: Daisuke Matsumoto, Kyoto (JP)

(73) Assignee: Arkray, Inc., Kyoto-Shi (JP)

( * ) Notice: Subject to any disclaimer, the term of this patent is extended or adjusted under 35 U.S.C. 154(b) by 609 days.

(21) Appl. No.: 11/664,207

(22) PCT Filed: Sep. 28, 2005

(86) PCT No.: PCT/JP2005/017813
§ 371 (c)(1),
(2), (4) Date: Mar. 29, 2007

(87) PCT Pub. No.: WO2006/035800
PCT Pub. Date: Apr. 6, 2006

(65) Prior Publication Data
US 2007/0292311 A1 Dec. 20, 2007

(30) Foreign Application Priority Data
Sep. 30, 2004 (JP) ................................ 2004-286629

(51) Int. Cl.
*C12Q 1/68* (2006.01)

(52) U.S. Cl. ......... 422/50; 422/82.05; 422/400; 422/91; 422/504; 219/541; 219/544; 219/528; 204/193; 204/400; 204/600

(58) Field of Classification Search .................. 219/216, 219/387, 541, 548
See application file for complete search history.

(56) References Cited

U.S. PATENT DOCUMENTS

| 4,801,784 A * | 1/1989 | Jensen et al. .................. 219/548 |
| 4,844,985 A | 7/1989 | Pharms et al. |
| 4,970,376 A | 11/1990 | Mellor et al. |
| 5,717,190 A | 2/1998 | Inoue |
| 5,922,591 A * | 7/1999 | Anderson et al. .......... 435/287.2 |
| 6,177,857 B1 * | 1/2001 | Inoue ........................... 338/22 R |
| 6,302,134 B1 * | 10/2001 | Kellogg et al. ................. 137/74 |
| 6,423,951 B1 * | 7/2002 | Elsasser ........................ 219/541 |
| 6,440,725 B1 | 8/2002 | Pourahmadi et al. |
| 7,009,180 B2 | 3/2006 | Sterling et al. |
| 7,189,367 B2 * | 3/2007 | Yamamoto et al. ........... 422/100 |

(Continued)

FOREIGN PATENT DOCUMENTS

| CN | 1259876 | 7/2000 |
| EP | 0 875 779 | 11/1998 |

(Continued)

OTHER PUBLICATIONS

International search Report from the corresponding PCT/JP2005/017813, mailed Jan. 17, 2006.

*Primary Examiner* — Sally Sakelaris
(74) *Attorney, Agent, or Firm* — Fox Rothschild LLP (57) ABSTRACT

The present invention relates to a thin film heater (2) including a thin film heat-producing resistor, and a first and a second thin film electrodes (22, 24) electrically connected to the thin film heat-producing resistor to apply voltage to the thin film heat-producing resistor. In the thin film heater (2), at least part of the thin film heat-producing resistor is light transmissive. Preferably, the first thin film electrode (22), the thin film heat-producing resistor and the second thin film electrode (24) are laminated in the film thickness direction in the mentioned order. The present invention further provides an analytical instrument (X) provided with the thin film heater (2).

20 Claims, 10 Drawing Sheets

U.S. PATENT DOCUMENTS

| | | | |
|---|---|---|---|
| 2002/0094303 A1* | 7/2002 | Yamamoto et al. | 422/100 |
| 2003/0223136 A1 | 12/2003 | Bade et al. | |
| 2006/0073600 A1 | 4/2006 | Kitamura | |
| 2009/0297402 A1 | 12/2009 | Kitamura | |

FOREIGN PATENT DOCUMENTS

| | | |
|---|---|---|
| EP | 1 500 937 | 1/2005 |
| JP | 49-69637 | 6/1974 |
| JP | 61-7709 | 1/1986 |
| JP | 7-14664 | 1/1995 |
| JP | 7-301750 | 11/1995 |
| JP | 8-114539 | 5/1996 |
| JP | 9-189703 | 7/1997 |
| JP | 9-304269 | 11/1997 |
| JP | 10-253536 | 9/1998 |
| JP | 2001-527220 | 12/2001 |
| JP | 2002/25757 | 1/2002 |
| JP | 2002-85961 | 3/2002 |
| JP | 2002-90357 | 3/2002 |
| JP | 2004-150805 | 5/2004 |
| JP | 2005-517923 | 6/2005 |
| WO | WO 03/093836 | 11/2003 |

* cited by examiner

THIN FILM HEATER AND ANALYTICAL INSTRUMENT

TECHNICAL FIELD

The present invention relates to a thin film heater, and an analytical instrument to be mounted in use to an analytical apparatus for analyzing a sample.

BACKGROUND ART

As an example of method for analyzing a sample, reaction liquid obtained by the reaction of the sample and a reagent is analyzed by an optical technique. Such an analysis is performed by mounting an analytical instrument for providing a reaction field to an analytical apparatus including an optical system capable of emitting and receiving light (See Patent Document 1, for example). In this case, to reduce the analysis error and enhance the reliability of the analysis result, it is desirable that the temperature of the analytical instrument (particularly reaction liquid) is controlled so that the sample reacts with the reagent substantially at the same temperature in each time of the measurement.

Figure 10A:
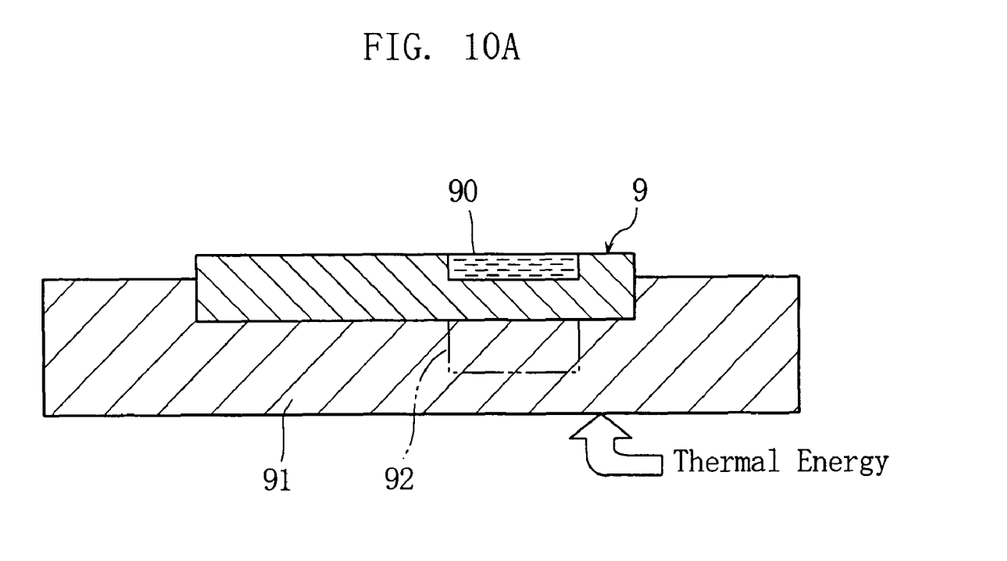
FIG. 10 is a sectional for describing a conventional temperature controlling method.
Figure 10B:
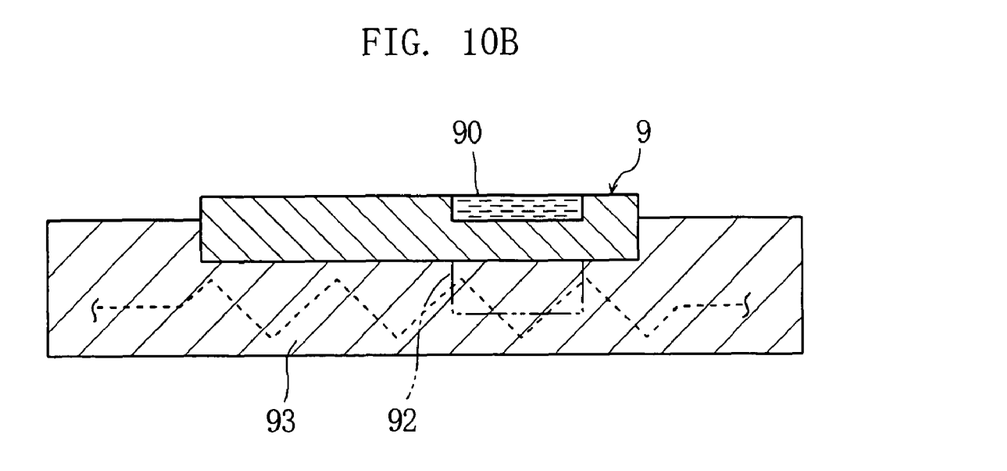

As shown in FIG. 10A, in a conventional method for controlling the temperature of the reaction liquid, an analytical instrument 9 is placed on a heat block 91 whose heat capacity is larger than that of the reaction liquid 90, and the temperature of the heat block 91 is controlled to control the temperature of the reaction liquid 90 (See Patent Documents 2 and 3, for example). In this method, the temperature of the reaction liquid is monitored by a temperature sensor 92 embedded in the heat block 91. When the temperature of the reaction liquid drops below a predetermined temperature, the heat block 91 is heated to raise the temperature of the reaction liquid via the heat block 91. As shown in FIG. 10B, in another method, the analytical instrument 9 is placed on a heating element 93 having a high temperature follow ability, and the temperature of the reaction liquid is controlled directly by the heating element 93 (See Patent Document 4, for example). In this method again, the temperature of the reaction liquid 90 is controlled by driving the heating element 93 in accordance with the monitoring results obtained by the temperature sensor 92.

In these temperature controlling methods, to raise the temperature of the reaction liquid 90, it is necessary to heat the heat block 91 or drive the heating element 93. Therefore, the power consumption is relatively large. Further, when the amount of the reaction liquid 90 is small as is in a microdevice, it is difficult to locally heat the region in which the reaction liquid 90 is retained by the heating medium such as the heat block 91 or the heating element 93. Therefore, to raise the temperature of the reaction liquid 90 with high responsiveness, the heating medium 91, 93 needs to be considerably larger than the region to be heated (the region directly below the reaction liquid 90 in the figures). Therefore, as compared with the heat quantity conducted from the heating medium 91, 93, the heat quantity utilized for raising the temperature of the reaction liquid 90 is small, so that the efficiency of use of the energy is low.

In this way, the conventional temperature control methods have a drawback that the power consumption is large. Therefore, it is difficult to apply the conventional temperature control methods to a small analytical apparatus driven by a small battery (like those generally used at home) incorporated as an internal power source in the apparatus. Even when the conventional methods are applied to such a small analytical apparatus, the operating time of the analytical apparatus becomes considerably short, so that the application is not practical. The operating time can be increased by increasing the capacity of the internal power source. In this case, however, the size of the analytical apparatus increases, whereby the portability is deteriorated. Although power may be supplied from an external power source, the use of external power source requires an adapter for connecting the analytical apparatus to the power source. Therefore, in the case of an analytical apparatus for portable use, the adapter needs to be carried, which deteriorates the portability and makes it difficult to use the apparatus away from home.

Patent Document 1: JP-A-H08-114539
Patent Document 2: JP-A-H09-189703
Patent Document 3: JP-A-H10-253536
Patent Document 4: JP-A-H09-304269

DISCLOSURE OF THE INVENTION

An object of the present invention is to provide an analytical instrument which is capable of heating a liquid component retained in the analytical instrument to a target temperature efficiently with small power consumption and without increasing the size of the analytical apparatus and to provide a thin film heater which can be applied to the analytical instrument.

According to a first aspect of the present invention, there is provided a thin film heater comprising a thin film heat-producing resistor, and a first and a second thin film electrodes electrically connected to the thin film heat-producing resistor to apply voltage to the thin film heat-producing resistor.

According to a second aspect of the present invention, there is provided an analytical instrument to be mounted in use to an analytical apparatus. The analytical instrument comprises at least one reaction vessel for causing reaction between a sample and a reagent, and a thin film heater which produces heat upon energization to heat an inside of said at least one reaction vessel. The thin film heater includes a thin film heat-producing resistor, and a first and a second thin film electrodes electrically connected to the thin film heat-producing resistor to apply voltage to the thin film heat-producing resistor.

For instance, at least part of the thin film heat-producing resistor is light transmissive. In this case, the thin film heat-producing resistor may be entirely transparent or formed with at least one through-hole or cutout for transmitting light.

For instance, the thin film heat-producing resistor may have a thickness of 20 to 300 nm. When the thickness is unduly small, the manufacture is difficult, which is disadvantageous in terms of the productivity and the manufacturing cost. When the thickness is unduly large, it may be difficult to obtain the intended resistance (amount of heat).

Preferably, the first thin film electrode, the thin film heat-producing resistor and the second thin film electrode are laminated in the film thickness direction in the mentioned order to form a heating laminate.

For instance, at least part of the heating laminate may be light transmissive. In the analytical instrument according to the present invention, the heating laminate is light transmissive at least at a portion corresponding to the reaction vessel. The heating laminate may be entirely transparent or formed with at least one through-hole or cutout for transmitting light.

When at least part of the heating laminate is light transmissive, it is preferable that the thin film heater further comprises a transparent substrate for supporting the heating laminate.

For instance, the heating laminate has a thickness of not more than 200 µm, and preferably, not more than 100 µm. When the thickness of the heating laminate is unduly large, the incorporation of the heating laminate in an analytical instrument hinders the size reduction of the analytical instrument.

In the analytical instrument according to the present invention, the thin film heat-producing resistor includes a portion which surrounds at least part of the periphery of the at least one reaction vessel as viewed in the film thickness direction.

For instance, the analytical instrument may be disk-shaped as a whole. In this case, the thin film heater is also disk-shaped as a whole.

For instance, the analytical instrument according to the present invention may further comprise a liquid receiving portion formed at the center thereof for retaining sample to be supplied to the at least one reaction vessel. In this case, a plurality of reaction vessels may be arranged along a common circumference around the liquid receiving portion, and the thin film heat-producing resistor has an annular shape including a through-hole at a location corresponding to the liquid receiving portion.

For instance, the analytical instrument according to the present invention comprises a first transparent member formed with a plurality of flow paths and a second transparent member bonded to the first transparent member to cover the flow paths. In this case, the heating laminate is provided on a surface of the first or the second transparent member. Preferably, the heating laminate is provided on a surface of the second transparent member which is opposite from a surface to which the first transparent member is bonded.

For instance, the analytical instrument may further comprise a third transparent member for covering the heating laminate. Preferably, the third transparent member is in the form of a cap capable of enclosing the second transparent member and the heating laminate between the third transparent member and the first transparent member.

For instance, the analytical instrument according to the present invention is mounted in use to an analytical apparatus provided with a first and a second probes for coming into contact with the first and the second thin film electrodes. In this case, the first and the second thin film electrodes are partially exposed for allowing the first and the second probes to come into contact with the first and the second thin film electrodes.

Preferably, the analytical instrument is so designed that the first and the second probes are capable of coming into contact with the first and the second thin film electrodes from a same side.

The analytical instrument according to the present invention may be a microdevice which uses a sample of not more than 400 μL, for example. For instance, when the analytical instrument includes a plurality of flow paths, the capacity of each of the flow paths may be 300 to 800 nL.

In the present invention, when the first thin film electrode, the thin film heat-producing resistor and the second thin film electrode are described as transparent, the term "transparent" is not limited to the state in which all the light rays in the visible light range are transmitted but also include the state in which the light of a particular wavelength is not absorbed or hardly absorbed, i.e., the optically transparent state with respect to a particular wavelength. For instance, in the analytical instrument of the present invention, when the light of a wavelength which is used for the analytical analysis using the analytical instrument is not absorbed by the heating laminate or is hardly absorbed by the heating laminate, the heating laminate is described as "transparent" even when it is not visually transparent.

BRIEF DESCRIPTION OF THE DRAWINGS

FIG. 7A is a plan view showing another example of thin film heater, whereas

FIG. 8A is a plan view showing another example of thin film heater, whereas

FIG. 9A is a plan view showing another example of thin film heater, whereas

BEST MODE FOR CARRYING OUT THE INVENTION

Figure 1:
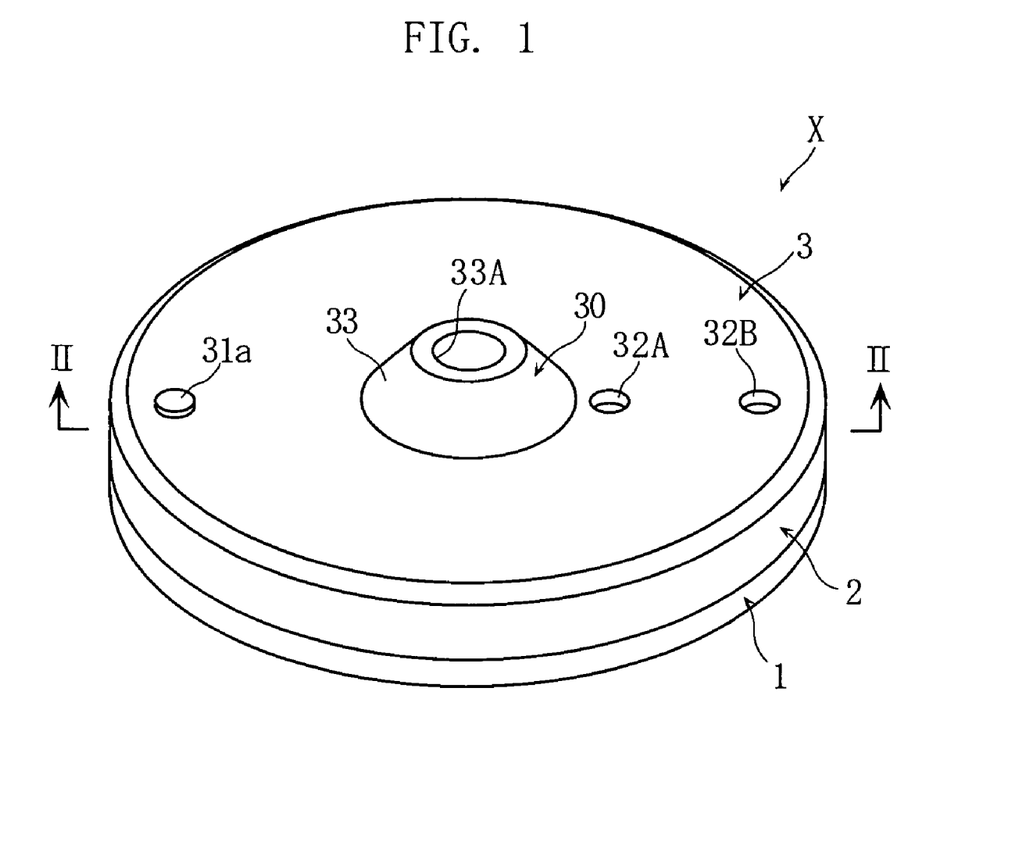
FIG. 1 is an overall perspective view showing an example of microdevice according to the present invention.
Figure 2:
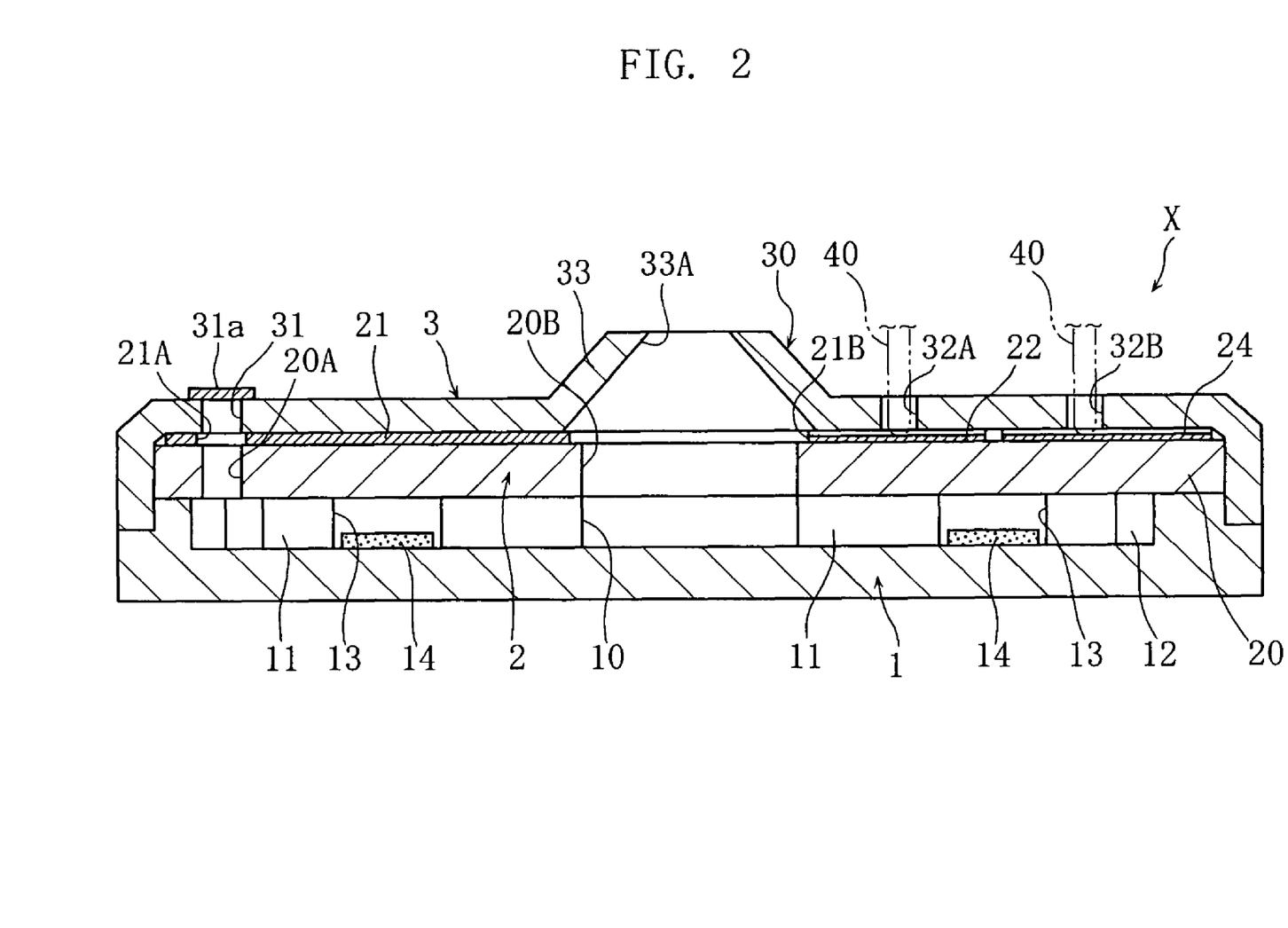
FIG. 2 is a sectional view taken along lines II-II in FIG. 1.
Figure 3:
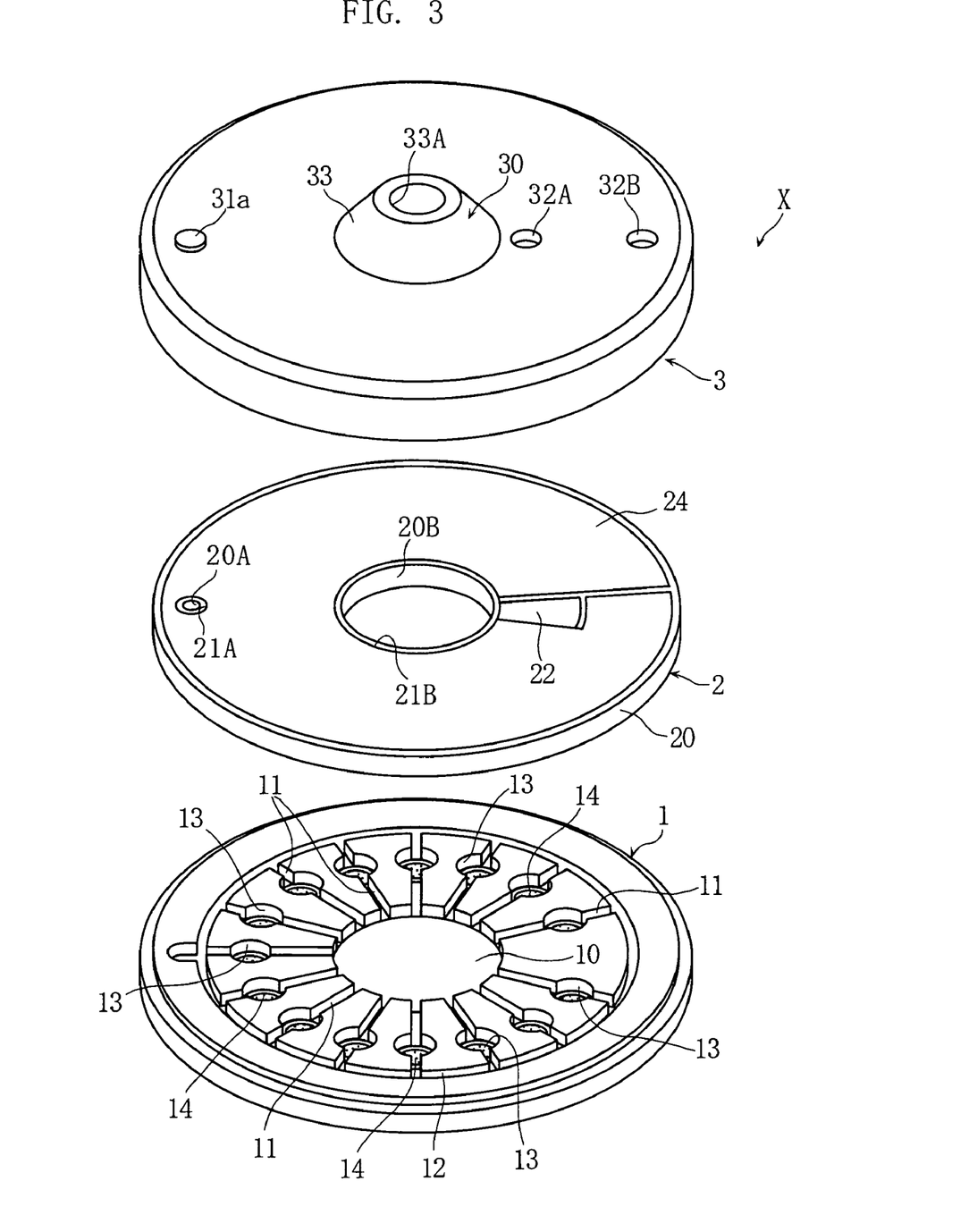
FIG. 3 is an exploded perspective view of the microdevice shown in FIG. 1.

FIGS. 1-3 show a microdevice X which is formed with a plurality of thin flow paths and which is in the form of a transparent disk as a whole. The microdevice X includes a substrate 1, a thin film heater 2 and a cap 3.

As better shown in FIGS. 2 and 3, the substrate 1 has a periphery formed with a step to have a reduced thickness, and a liquid receiving portion 10, a plurality of flow paths 11 and a common flow path 12 are formed in the substrate 1. As a whole, however, the substrate is in the form of a transparent disk.

The liquid receiving portion 10 serves to retain a sample to be introduced into each of the flow paths 11. The liquid receiving portion 10 comprises a columnar recess formed at the center of the substrate 1.

The flow paths 11 are utilized for moving a sample and extend from the liquid receiving portion 10 toward the periphery of the substrate 1. The flow paths 11 extend radially as a whole. Each of the flow paths 11 includes a reaction vessel 13 for causing reaction between the sample and a reagent, so that a plurality of reaction vessels 13 are provided in the substrate 1. The reaction vessels 13 are positioned at the same distance from the liquid receiving portion 13 and arranged along a common circumference in the substrate 1. Each of the reaction vessels 13 is formed with a reagent portion 14. The reagent portion 14 is in a solid state to be soluble when a sample is supplied thereto. The reagent portion develops a color upon reaction with a detection target component contained in the sample. In this embodiment, a plurality of kinds of reagent portions 14 which differ from each other in component or composition are provided so that the microdevice X can measure a plurality of items.

The common flow path 12 is utilized for discharging gas existing in the flow paths 11 to the outside. The common flow path 12 comprises an annular groove formed at a the periphery of the substrate and communicates with the flow paths 11.

The substrate 1 having the above-described structure can be formed by molding an acrylic resin such as polymethyl methacrylate (PMMA) or a transparent resin such as polydimethylsiloxane (PDMS). By appropriately designing the shape of a mold, the liquid receiving portion 10, the flow paths 11 and the common flow path 12 can be formed at the same time in the resin molding process.

The thin film heater 2 serves to heat the inside of each of the reaction vessels 13 and includes a sub substrate 20 and a heating laminate 21.

The sub substrate 20 is in the form of a transparent disk which is slightly smaller than the substrate 1. The sub substrate 20 is formed with through-holes 20A and 20B. The through-hole 20A is utilized for discharging the gas existing in the common flow path 12 of the substrate 1 to the outside and formed at a peripheral portion of the sub substrate 20 so as to communicate with the common flow path 12. The through-hole 20B is utilized for introducing a sample into the liquid receiving portion 10 of the substrate 1 and formed at the center of the sub substrate 20 so as to communicate with the liquid receiving portion 10.

Figure 4:
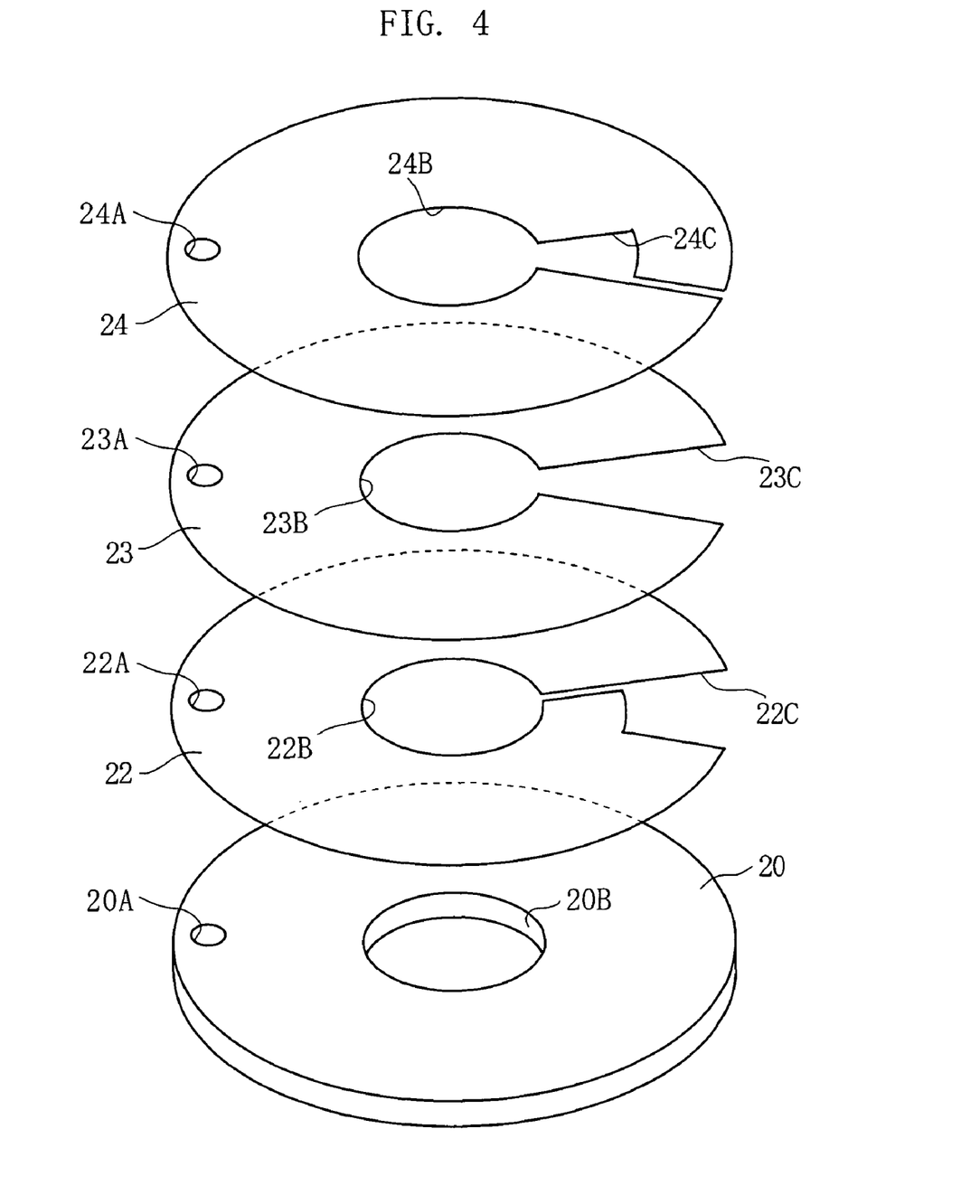
FIG. 4 is an exploded perspective view of a heater of the microdevice shown in FIG. 1.

The heating laminate 21 generates heat due to the electrical resistance when power is supplied. The heating laminate 21 is arranged on the sub substrate 20 and formed with through-holes 21A and 21B at locations corresponding to the through-holes 20A and 20B of the sub substrate 20. As shown in FIG. 4, the heating laminate comprises a thin film anode 22, a thin film heat-producing resistor 23 and a thin film cathode 24 which are laminated in the mentioned order on the sub substrate 20.

As shown in FIGS. 2 and 3, the through-hole 21A serves to allow the gas existing in the common flow path 12 of the substrate 1 to be discharged to the outside. The through-hole 21B serves to allow the sample to be introduced into the liquid receiving portion 10 of the substrate 1.

As shown in FIGS. 2-5, the thin film anode 22, the thin film heat-producing resistor 23 and the thin film cathode 24 are formed with through-holes 22A-24A and 22B-24B, and have a generally annular configuration partially cut away by the provision of the cutouts 22C-24C. The through-holes 22A-24A constitute the through-hole 21A of the heating laminate 21, whereas the through-holes 22B-24B constitute the through-hole 21B of the heating laminate 21.

The thin film anode 22 and the thin film cathode 24 are transparent and utilized for applying a voltage to the thin film heat-producing resistor 23. The electrodes 22 and 24 are exposed via probe insertion ports 32A and 32B of the cap 3, which will be described later, so that voltage application probes 40 and 41 of an analytical apparatus (not shown) can be brought into contact with the electrodes through the probe insertion ports 32A and 32B.

The thin film heat-producing resistor 23 is transparent and heated by the application of a voltage using the thin film anode 22 and the thin film cathode 24. Herein, the term "transparent" means the state in which at least the light of a wavelength used for the analysis with the analytical instrument is not absorbed or is hardly absorbed and does not necessarily mean the visually transparent state.

Each of the thin film anode 22, the thin film heat-producing resistor 23 and the thin film cathode 24 can be formed as a transparent thin film having an appropriate resistance by selecting the film forming method, the thickness or the material. The thin film heat-producing resistor 23 is so formed as to have a higher sheet resistance than those of the thin film anode 22 and the thin film cathode 24.

For instance, each of the thin film anode 22 and the thin film cathode 24 has a thickness of 1 to 100 μm, whereas the thin film heat-producing resistor 23 has a thickness of 20 to 300 nm. As a method for forming the thin films 22-24, screen printing, sputtering, CVD, vapor deposition, application or rolling may be employed. As the material of the thin films 22-24, use may be made of inorganic oxide, an inorganic substance such as TiN or an organic substance such as conductive polymer. Examples of inorganic oxide include an oxide of a single element such as $In_2O_3$, $ZnO$, $SnO_2$, a complex oxide obtained by compounding two or more oxides of a single element selected from the above examples, or an oxide obtained by doping an oxide of a single element or a complex oxide with a particular element. As the dopant, use may be made of B, $Al_2O_3$ or $Ga_2O_3$, for example. The thin film anode 22 and the thin film cathode 24 may be formed by working a highly conductive metal (e.g. noble metal such as gold) into a thin metal film in the order of nm to have a light transmittance.

As shown in FIGS. 1-3, the cap 3 is formed with a sample introduction port 30, a gas discharge port 31 and probe insertion ports 32A and 32B. The cap is in the form of a transparent disk as a whole.

The sample introduction port 30 is utilized for introducing a sample. The sample introduction port 30 is provided by forming a bulging portion 30 having an opening 33A at the center of the cap 3. The opening 33A communicates with the liquid receiving portion 10 of the substrate 1 via the through-holes 20B, 21B of the sub substrate 20 and the heating laminate 21. With this structure, the sample can be introduced into the liquid receiving portion 10 through the sample introduction port 30 (opening 33A).

The gas discharge port 31 is utilized for discharging the gas existing in the flow paths 11 to the outside through the common flow path 12. The gas discharge port 31 is a through-hole communicating with the common flow path 12 via the through-holes 20A, 21A of the sub substrate 20 and the heating laminate 21. Before the use of the microdevice 1, the gas discharge port 31 is closed by a sealing member 31a. For instance, the sealing member 31a is peeled off when the microdevice X is to be used. By peeling off the sealing member, the gas discharge port 31 is opened so that the flow paths 11 communicate with the outside through the common flow path 12. Alternatively, the gas discharge port 31 may be opened by forming a hole in the sealing member 31a. Specifically, the sealing member 31a may be made of a thin film such as an aluminum foil, and a hole may be formed in the sealing member 31a by piercing the sealing member 31a with a needle or the like. Alternatively, the sealing member 31a may be made of a thermoplastic resin having a low melting point (not higher than 100 degrees, for example), and a hole may be formed in the sealing member 31a by irradiating the sealing member 31a with laser beam.

The probe insertion holes 32A and 32B are through-holes into which the voltage application probes 40 and 41 of the analytical apparatus are to be inserted for coming into contact with the thin film anode 22 and the thin film cathode 24 of the thin film heater 2.

Similarly to the substrate 1, the cover 3 having the above-described structure can be formed by molding a transparent resin. The sample introduction port 30, the gas discharge port 31 and the probe insertion ports 32A, 32B can be formed at the same time in the resin molding process.

The use and advantages of the microdevice X will be described below.

To analyze a sample, the microdevice X is mounted to an analytical apparatus (not shown). The sample may be supplied to the microdevice X in advance or supplied to the microdevice X after the microdevice X is mounted to the analytical apparatus.

The supply of the sample to the microdevice X is performed through the sample introduction port 30 of the cap 3. The sample introduced through the sample introduction port 30 reaches the liquid receiving portion 10 through the through-holes 20B, 21B of the sub substrate 20 and the heating laminate 21. However, since the gas discharge port 31 of the microdevice X is closed by the sealing member 31a, capillary force is not exerted to the inside of each of the flow paths 11. Therefore, the sample is retained in the liquid receiving portion 10.

When the microdevice X is mounted to the analytical apparatus (not shown), the voltage application probes 40 and 41 of the analytical apparatus are brought into contact with the thin film anode 22 and the thin film cathode 24 through the probe insertion ports 32A and 32B of the cap 3. The analytical apparatus (not shown) applies a voltage across the thin film anode 22 and the thin film cathode 24 of the thin film heater 2 via the probes 40 and 41. As a result, the thin film heat-producing resistor 23 is energized to generate heat, whereby the reaction vessels 13 are heated. The heating of the reaction vessels 13 is performed under feedback control in which the temperature of the reaction vessel 13 is monitored to maintain the temperature of the reaction vessels 13 at a target temperature or by applying a predetermined voltage for a predetermined time period.

Subsequently, the gas discharge port 31 is opened so that the sample retained in the liquid receiving portion 10 flows into each of the flow paths 11. As noted before, the gas discharge port 31 is opened by peeling off the sealing member 31a or making a hole in the sealing member 31a.

When the gas discharge port 31 is opened, the inside of each of the flow paths 22 communicates via the common flow path 12 and the gas discharge port 31. As a result, capillary force is exerted on each of the flow paths 11, so that the sample retained in the liquid receiving portion 10 moves through the flow paths 11 to reach the reaction vessels 13. In each of the reaction vessels 13, the reagent portion 14 is dissolved by the sample, whereby a liquid phase reaction system is established. The liquid phase reaction system is heated to a target temperature by heating the reaction vessel 13 by the thin film heater 2. In the liquid phase reaction system, the sample reacts with the reagent. As a result, the liquid phase reaction system develops a color related with the amount of the detection target component contained in the sample, or a reaction product corresponding to the amount of the detection target component is produced. As a result, the liquid phase reaction system of the reaction vessel 13 shows a light transmittance (light absorbance) corresponding to the amount of the detection target component.

When a predetermined period has elapsed after the supply of the sample to each of the reaction vessels 13, photometry is performed with respect to the liquid phase reaction system in the reaction vessels 13 in a predetermined order. In the analytical apparatus (not shown), computation necessary for the analysis of the detection target component in the sample is performed based on the photometry results of each of the reaction vessels 13.

According to the present invention, the reaction vessels 13 are heated by the thin film heater 2 incorporated in the microdevice X. The design of the thin film heater 2 can be varied in accordance with the size, position, number or shape of the reaction vessels of the microdevice X. Therefore, only the liquid phase reaction system in the reaction vessels 13 can be selectively heated, so that the supplied energy can be used efficiently. Further, since the thin film heater 2 can be provided adjacent to the reaction vessels 13, thermal energy can be efficiently transferred from the thin film heater 2 to the liquid phase reaction system. Therefore, the efficiency of use of the supplied energy can be enhanced, and the power consumption by the heating of the liquid phase reaction system (reaction vessels 13) can be reduced. Therefore, as the internal power source for driving the thin film heater 2, a small battery such as a dry cell generally used at home can be used. Even when such a small battery is used, the battery can sufficiently heat the liquid phase reaction system (reaction vessels 13) without running down quickly. Therefore, even in a small analytical apparatus, the liquid phase reaction system (reaction vessels 13) can be heated by utilizing the internal power source and without increasing the size of the analytical apparatus. Since the internal power source can be used, connection with an external power source is not necessary, so that an adapter is not necessary. Accordingly, in carrying the analytical apparatus, it is unnecessary to carry an adapter, whereby the portability is improved.

The present invention is not limited to the foregoing embodiment and may be varied in design in various ways. For instance, firstly, the analytical instrument according to the present invention does not necessarily need to be structured as a microdevice. Secondly, the analytical instrument is not limited to one designed to perform the sample analysis by an optical method but may be designed to perform the sample analysis by an electrochemical method. Thirdly, the analytical instrument is not limited to one provided with a plurality of reaction vessels. The heater of the analytical instrument according to the present invention may have such structures as shown in FIGS. 6-9.

Figure 5:
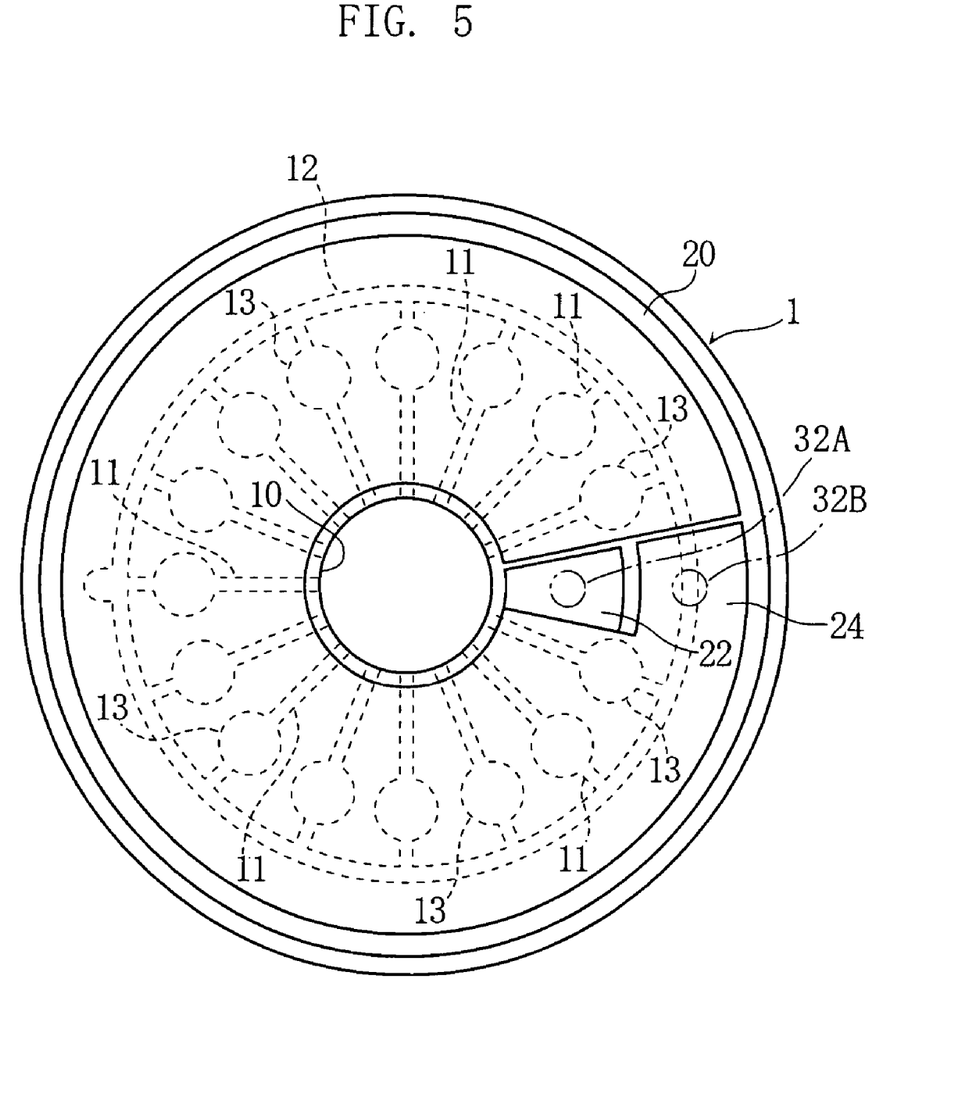
FIG. 5 is a plan view of the microdevice shown in FIG. 1 in a state in which the cap is removed.
Figure 6:
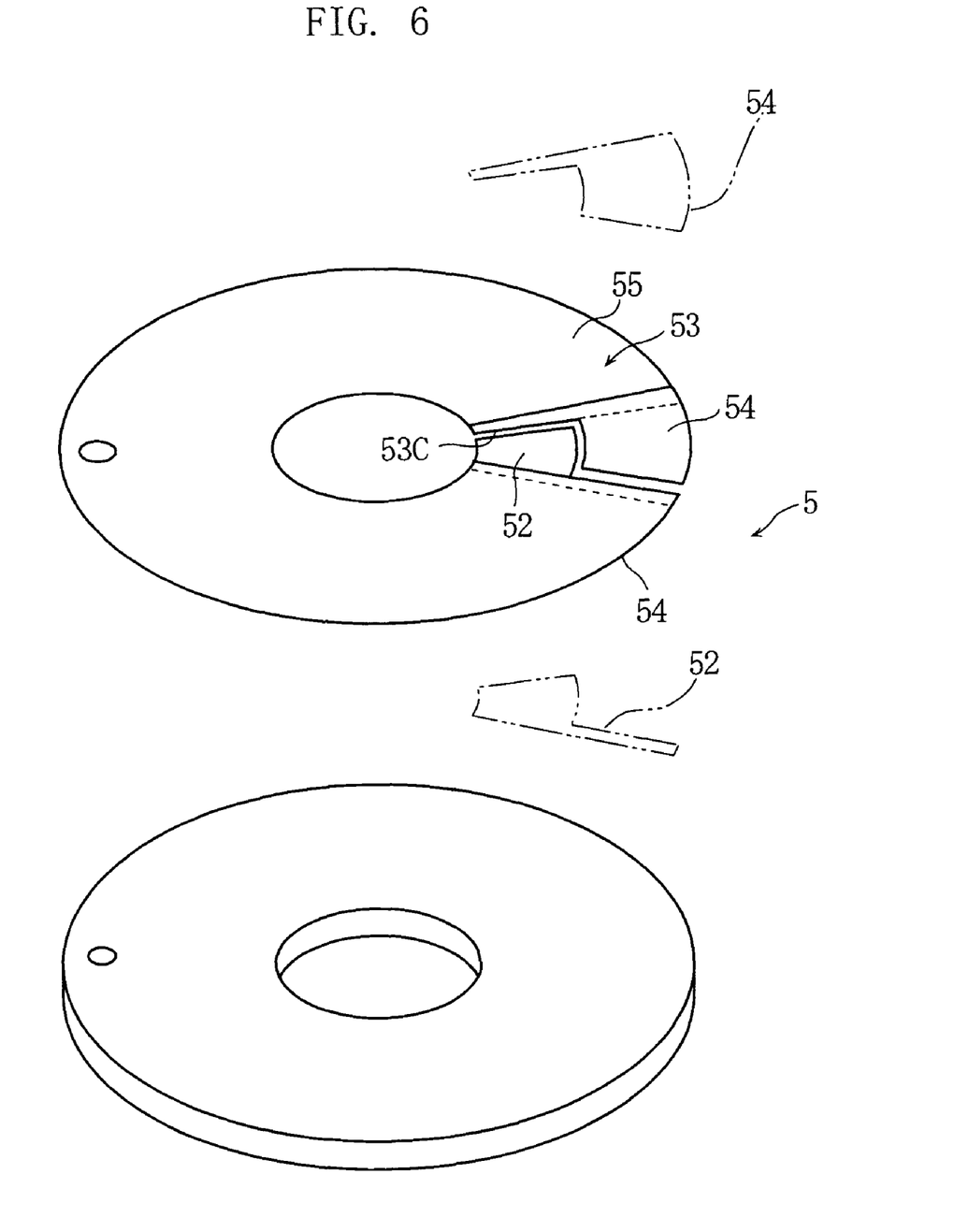
FIG. 6 is an exploded perspective view showing another example of thin film heater according to the present invention.

The heater 5 shown in FIG. 6 is similar in structure to the foregoing thin film heater 2 (See FIGS. 4 and 5) in that the heater includes a thin film anode 52, a thin film heat-producing resistor 53 and a thin film cathode 54. However, the heater 5 differs from the thin film heater 2 (See FIGS. 4 and 5) in that the thin film anode 52 and the thin film cathode 54 are electrically connected selectively to the portions (ends) of the thin film heat-producing resistor 53 at which a cutout 53 is formed.

In the heater 5 shown in FIG. 6, the thin film anode 52 is connected to the lower surface 54 of the thin film heat-producing resistor 53, whereas the thin film cathode 54 is connected to the upper surface 55 of the thin film heat-producing resistor 53. However, the thin film anode 52 and the thin film cathode 54 may be connected to a same surface of the thin film heat-producing resistor 53.

Figure 7A:
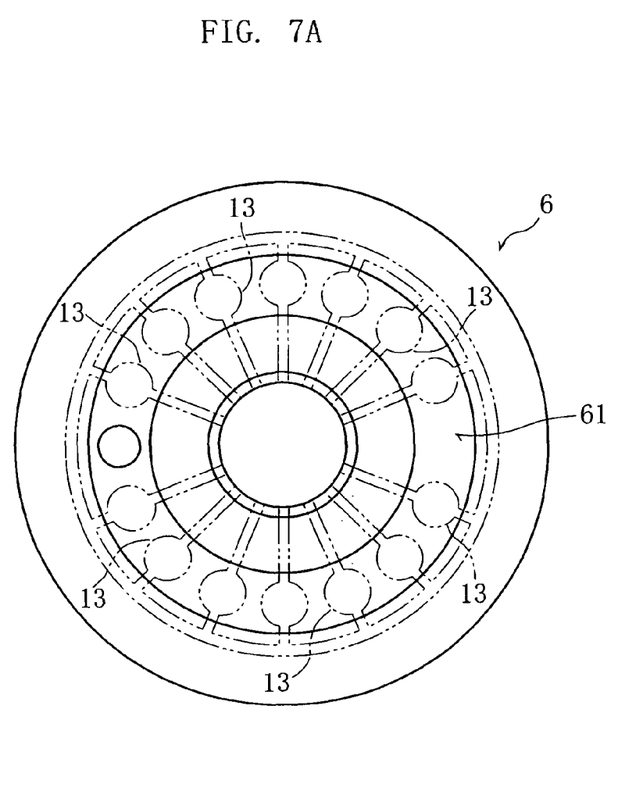
Figure 7B:
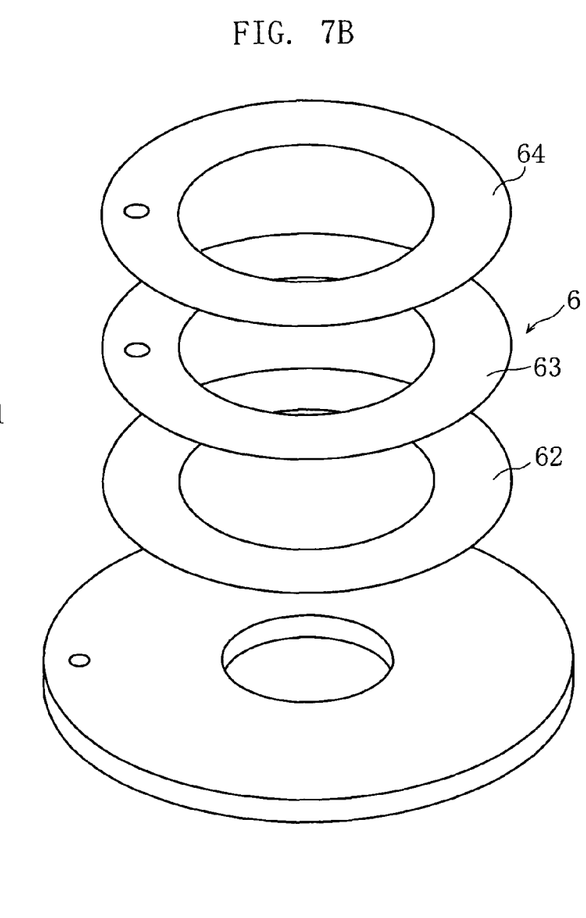
FIG. 7B is the exploded perspective view.

The heater 6 shown in FIGS. 7A and 7B includes a heating laminate 61 having a configuration obtained by eliminating the cutouts 22C-24C (See FIGS. 4 and 5) from the heating laminate 21 of the thin film heater 2. Specifically, the heating laminate 61 includes a thin film anode 62, a thin film heat-producing resistor 63 and a thin film cathode 64 each of which is shaped like a doughnut. The dimension (difference between the inner diameter and the outer diameter) of each of the thin films 62-64 is smaller than that of the thin films 22-24 (See FIGS. 4 and 5) of the thin film heater 2 so that the thin films 62-64 selectively cover the portion provided with the reaction vessels 13.

Since the area to be heated is relatively small in this structure, efficient heating is possible, and the running cost can be reduced. Further, since the dimension of the thin films 62-64 is small, the cost for the material can also be reduced.

Figure 8A:
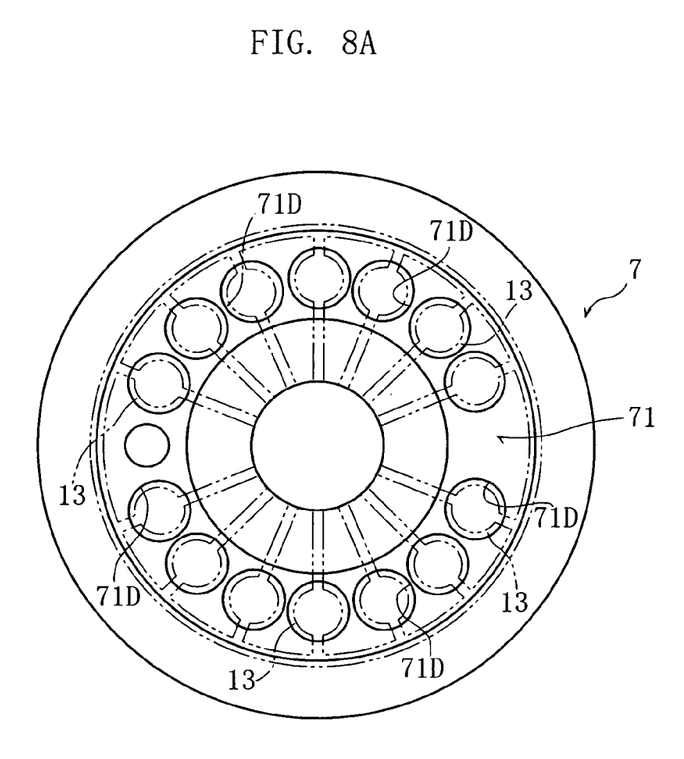
Figure 8B:
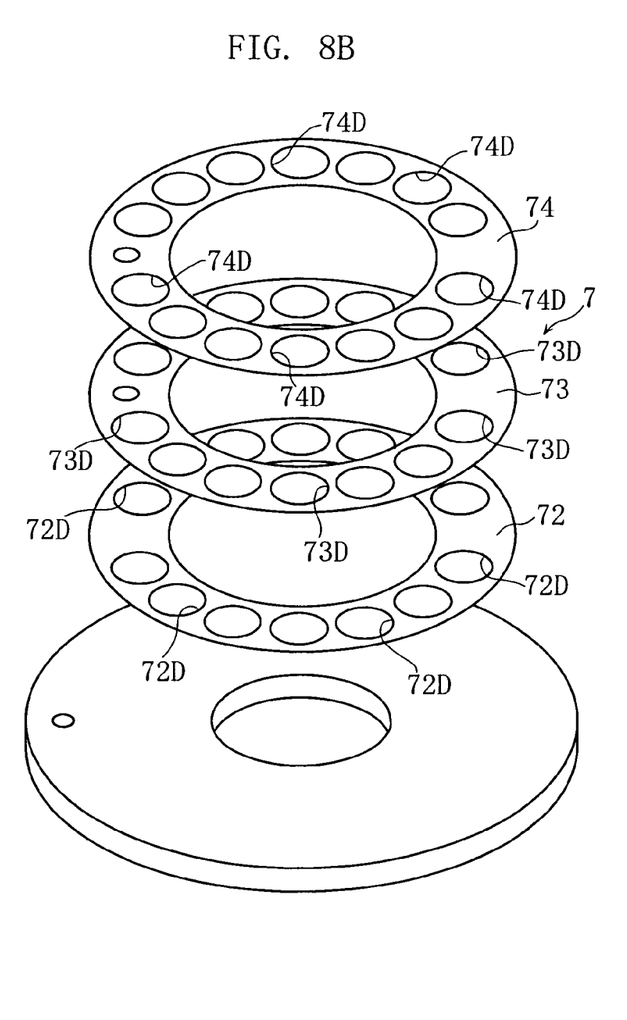
FIG. 8B is the exploded perspective view.

The heater 7 shown in FIGS. 8A and 8B has a structure obtained by adding a plurality of through-holes 71D to the heater 6 shown in FIG. 6. Specifically, the through-holes 71D are provided in the heating laminate 71 at locations corresponding to the reaction vessels 13. Each of the through-holes 71D is made up of through-holes 72D, 73D and 74D respectively formed in the thin film anode 72, the thin film heat-producing resistor 73 and the thin film cathode 74 at locations corresponding to the reaction vessel 13.

With this structure, since the through-holes 71D are provided in the heating laminate 71 at locations corresponding to the reaction vessels 13, the heating laminate 71 and hence the thin films 72-74 do not need to be transparent. Therefore, the material for forming the heating laminate 71 and the thin films 72-74 can be selected from a wide range, whereby the manufacturing cost can be reduced.

Figure 9A:
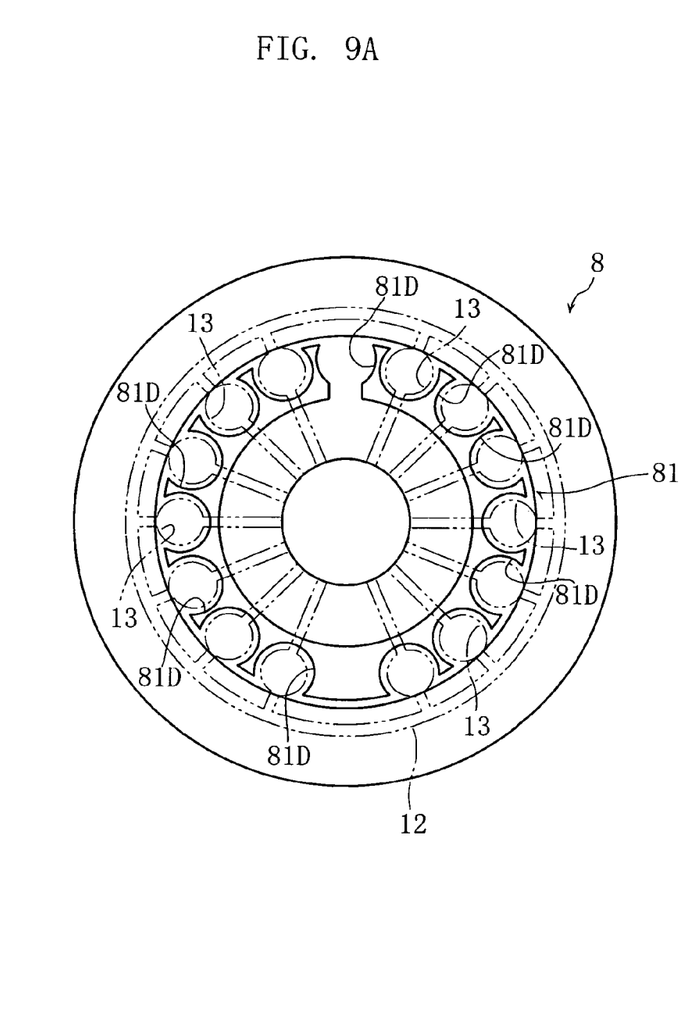
Figure 9B:
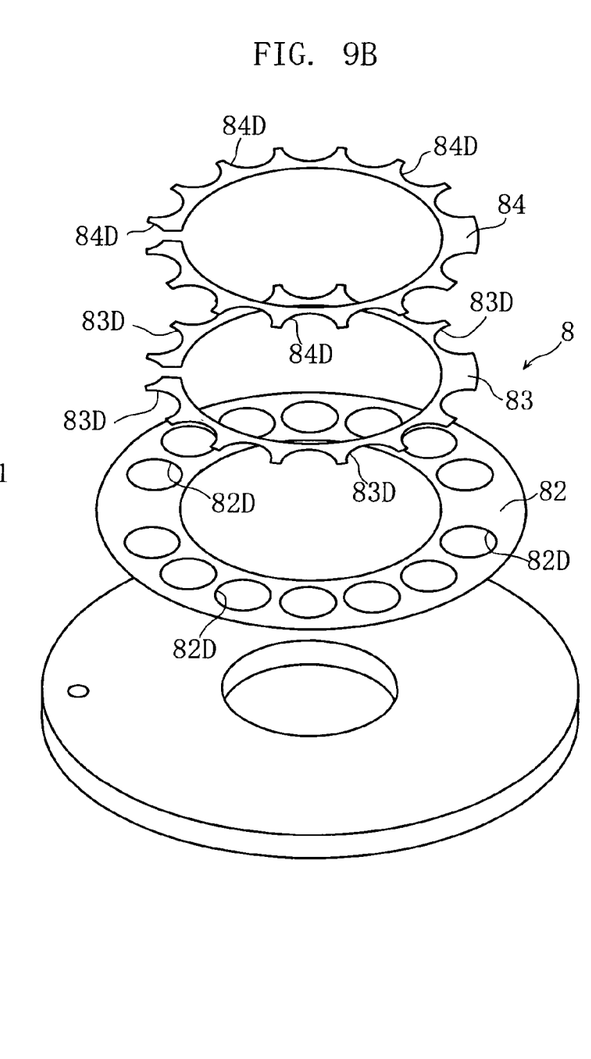
FIG. 9B is the exploded perspective view.

Similarly to the heater 7 shown in FIG. 8, the heater 8 shown in FIGS. 9A and 9B includes a plurality of through-holes 81D in the heating laminate 81 at locations corresponding to the reaction vessels 13. The through-holes 81D are provided by forming a plurality of through-holes 82D in the thin film anode 82 at locations corresponding to the reaction vessels 13 and forming a plurality of cutouts 83D and 84D respectively in the thin film heat-producing resistor 83 and the thin film cathode 84 at locations corresponding to the reaction vessels 13. With this structure, the heating of each of the reaction vessels 13 by the heating laminate 81 is performed not at the entire circumference of the reaction vessel 13 but at a portion adjacent to the common flow path 12. It is to be noted that the thin film anode 82 may have the same configuration as that of the thin film heating resistor 83 and the thin film cathode 84.

In the heaters 6-8 shown in FIGS. 7-9, each of the thin films may be partially cut away similarly to the thin film heater 2 shown in FIGS. 4 and 5. Further, similarly to the heater 5 shown in FIG. 6, the thin film heat-producing resistor may be partially cut away, and the thin film anode and the thin film cathode may be electrically connected selectively to the opposite ends of the thin film heat-producing resistor, respectively.

The invention claimed is:

1. An analytical instrument to be mounted in use to an analytical apparatus, the analytical instrument comprising at least one reaction vessel for causing reaction between a sample and a reagent, and a thin film heater that when energized, provides heat to an inside of said at least one reaction vessel;
    wherein the thin film heater includes a thin film heat-producing resistor, and a first and a second thin film electrodes electrically connected to the thin film heat-producing resistor to apply voltage to the thin film heat-producing resistor;
    wherein the first thin film electrode, the thin film heat-producing resistor and the second thin film electrode are laminated in a film thickness direction in the mentioned order to form a heating laminate in which the first thin film electrode is formed on a first surface of the thin film heat-producing resistor while the second thin film electrode is formed on a second surface of the thin film heat-producing resistor opposite to the first surface of the thin film heat-producing resistor;
    wherein the thin film heat-producing resistor is generally annular and includes an inner circumferential edge and an outer circumferential edge, the thin film heat-producing resistor also including a radially extending cutout that extends from the inner circumferential edge to the outer circumferential edge, one of the first and second thin film electrodes including a first projection located at the radially extending cutout of the thin film heat-producing resistor closer to the inner circumferential edge, the other of the first and second thin film electrodes including a second projection located at the radially extending cutout of the thin film heat-producing resistor closer to the outer circumferential edge, the first and second projections being radially separated from each other at the radially extending cutout of the thin film heat-producing resistor.

2. The analytical instrument according to claim 1, wherein at least part of the thin film heater is light transmissive.

3. The analytical instrument according to claim 2, wherein the thin film heater is entirely transparent.

4. The analytical instrument according to claim 2, wherein the thin film heater includes at least one through-hole or cutout for transmitting light.

5. The analytical instrument according to claim 1, wherein the thin film heat-producing resistor has a thickness of 20 to 300 nm.

6. The analytical instrument according to claim 1, wherein the thin film heat-producing resistor includes a portion which surrounds at least part of a periphery of said at least one reaction vessel as viewed in a film thickness direction.

7. The analytical instrument according to claim 6, wherein the analytical instrument is disk-shaped as a whole and further comprises a liquid receiving portion formed at a center thereof for retaining sample to be supplied to said at least one reaction vessel; wherein the analytical instrument includes a plurality of reaction vessels arranged along a common circumference around the liquid receiving portion; and
    wherein the thin film heater has an annular shape including a through-hole at a location corresponding to the liquid receiving portion.

8. The analytical instrument according to claim 1, wherein the heating laminate is light transmissive at least at portions corresponding to the reaction vessels.

9. The analytical instrument according to claim 8, wherein the heating laminate is entirely transparent.

10. The analytical instrument according to claim 8, wherein the heating laminate includes a plurality of through-holes or cutouts to transmit light at locations corresponding to the reaction vessels.

11. The analytical instrument according to claim 8, further comprising a transparent substrate for supporting the heating laminate.

12. The analytical instrument according to claim 1, wherein the heating laminate has a thickness of not more than 200 μm.

13. The analytical instrument according to claim 12, wherein the heating laminate has a thickness of not more than 100 μm.

14. The analytical instrument according to claim 1, comprising a first transparent member formed with a plurality of flow paths and a second transparent member bonded to the first transparent member to cover the flow paths;
    wherein the heating laminate is provided on a surface of the first or the second transparent member.

15. The analytical instrument according to claim 14, wherein the heating laminate is provided on a surface of the second transparent member which is opposite from a surface to which the first transparent member is bonded; and
    wherein the analytical instrument further comprises a third transparent member for covering the heating laminate.

16. The analytical instrument according to claim 15, wherein the third transparent member is in a form of a cap capable of enclosing the second transparent member and the heating laminate between the third transparent member and the first transparent member.

17. The analytical instrument according to claim 1, wherein the analytical instrument is mounted in use to an analytical apparatus provided with a first and a second probes for coming into contact with the first and the second thin film electrodes; and wherein the first and the second thin film electrodes are partially exposed for allowing the first and the second probes to come into contact with the first and the second thin film electrodes.

18. The analytical instrument according to claim 17, wherein the analytical instrument is so designed that the first and the second probes are capable of coming into contact with the first and the second thin film electrodes from a same side.

19. The analytical instrument according to claim 1, wherein the analytical instrument is a microdevice which uses a sample of not more than 400 µL.

20. The analytical instrument according to claim 1, wherein said at least one reaction vessel communicates with a gas discharge port formed in a cap covering the heating laminate, the heating laminate being formed with a through-hole corresponding to the gas discharge port.

* * * * *